United States Patent [19]
Mark et al.

[11] Patent Number: 5,214,062
[45] Date of Patent: May 25, 1993

[54] METHOD AND COMPOSITION FOR TREATING IMMUNE DISORDERS, INFLAMMATION AND CHRONIC INFECTIONS

[75] Inventors: David A. Mark, Oak Park; W. Bruce Rowe, Evanston, both of Ill.

[73] Assignee: Clintec Nutrition Co., Deerfield, Ill.

[21] Appl. No.: 865,288

[22] Filed: Apr. 8, 1992

[51] Int. Cl.$^5$ ............................................. A61K 31/38
[52] U.S. Cl. .................... 514/369; 514/560; 514/18
[58] Field of Search ............ 514/560, 369, 18

[56] References Cited

U.S. PATENT DOCUMENTS

| | | | |
|---|---|---|---|
| 4,775,675 | 10/1988 | Györgydeák et al. | 514/369 |
| 5,053,387 | 10/1991 | Alexander | 514/560 |
| 5,089,268 | 2/1992 | Katz | 514/560 |

Primary Examiner—Marianne M. Cintins
Assistant Examiner—John Peabody

[57] ABSTRACT

The present invention provides a method of treating a viral infection or immune disorder as well as a composition for same. The method of treatment comprises administering to a patient having a viral infection or immune disorder a therapeutically effective amount of a composition including an intracellular glutathione stimulator and an omega-3 fatty acid source.

5 Claims, 1 Drawing Sheet

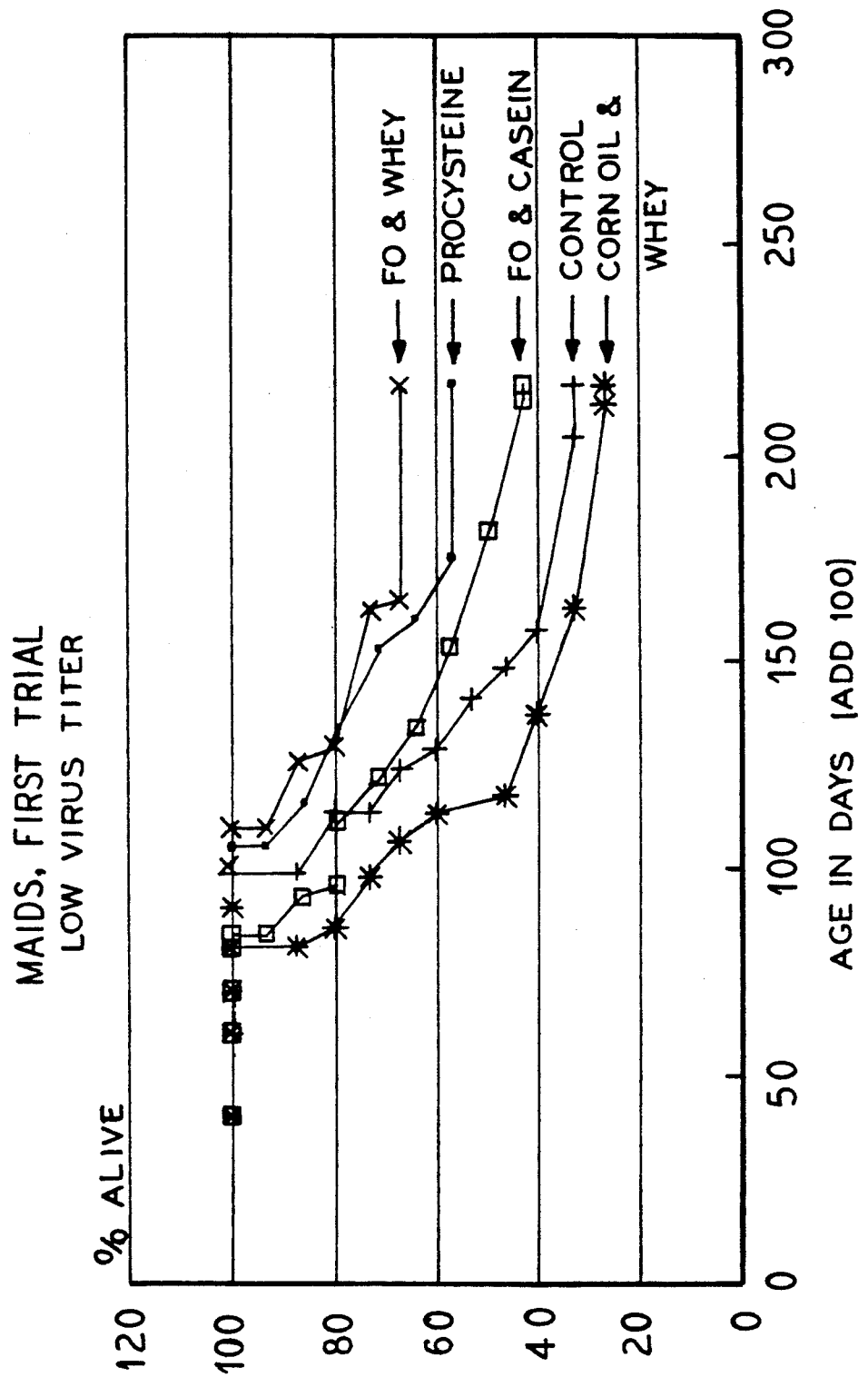

METHOD AND COMPOSITION FOR TREATING IMMUNE DISORDERS, INFLAMMATION AND CHRONIC INFECTIONS

BACKGROUND OF THE INVENTION

The present invention relates to compositions and methods for treating disease states. More specifically, the present invention relates to compositions and methods for treating immune disorders, inflammation, and chronic infections.

Immune disorders comprise a group of conditions, characterized clinically by an increased susceptibility to infections. As a result, severe acute, recurrent, and chronic disease can occur which results from one or more defects in the immune system. See the Merck Manual, Fifteenth Edition.

Autoimmune disorders relate to disorders in which the immune system produces autoantibodies to an endogenous antigen, with consequent injury to tissues. See the Merck Manual, Fifteenth Edition, page 319. The Merck Manual lists the following disorders as being highly probable of an autoimmune disorder: Hashimoto's thyroiditis; Systemic lupus erythematosus; Goodpasture's syndrome; Pemphigus; Receptor autoimmunity, Graves' disease, Myasthenia gravis, and Insulin resistance; autoimmune hemolytic anemia; and autoimmune thrombocytopenic purpura. The following disorders are listed as probable of an autoimmune disorder: Rheumatoid arthritis; Progressive systemic sclerosis; Mixed connective tissue disease; Polymyositis; Pernicious anemia; Idiopathic Addison's disease; Infertility (some cases); Glomerulonephritis; Bullous pemphigoid; Sjorgren's syndrome; Diabetes mellitus (some); and Adrenergic drug resistance (some asthmatics).

The following disorders are listed as possible of an autoimmune disorder: Chronic active hepatitis; Primary biliary cirrhosis; Other endocrine gland failure; Vitiligo; Vasculitis; Post-myocardial infarction, cardiotomy syndrome; Urticaria, atopic dermatitis, asthma (some cases); and Many other inflammatory, granulomatous, degenerative, and atrophic disorders.

Viral infections, as the name implies, results from an infection from a viral agent.

Acute viral infections result from exposure of the host to an infectious viral agent. The nature and clinical symptoms associated with the infection will vary depending upon the virus present. In many non-lethal acute viral infections, the host organism will mount an effective immune response to the invading virus and eventually clear the virus from its system entirely. Other viruses establish chronic infections in which viral replication and associated symptomatology occur continuously throughout the life of the host organism.

A smaller number of viruses, however, establish a different life cycle pattern. Infections caused by these viruses are marked by an initial, occasionally asymptomatic infection during which viral replication occurs. This is followed by a period in which infectious viral particles are not produced. The viral genome remains within the cells of its host organism but does not replicate. This period of persistent, but non-active, infection has been termed latent viral infection.

Viral latency has been clearly described among members of the Herpetoviridae family. There are six presently known herpes viruses: HSV-1; HSV-2; VZV; EBV; CMV; and HHV-6. It also appears probable that HIV-1, the virus responsible for Acquired Immunodeficiency Syndrome (AIDS) in humans, undergoes a period of latent activity. Schnittman, et al, *The Reservoir for HIV-1 in Human Peripheral Blood is a T Cell That Maintains Expression of CD4*, Science, Vol. 245, pp. 305–308, 1989.

Of clinical significance is the finding that this latent virus can, upon appropriate stimulation, reactivate. Reactivation gives rise to both the production of infectious viral particles and the appearance of symptomatology associated with recurrent infection. A variety of stimuli have been reported to reactivate latent viruses, including (but not limited to): fever; local trauma; exposure to sunlight or exogenous chemicals (including some medications); trigeminal nerve manipulation; menstruation; malnutrition; physical or emotional stress; concurrent infections with other pathogens; and alterations in immune status.

U.S. patent application Ser. No. 07/769,194 entitled: "METHOD FOR TREATMENT OF LATENT VIRUS INFECTIONS" discloses a method for treating a latent viral infection comprising the steps of administering a non-cysteine substrate that stimulates the intracellular synthesis of glutathione.

SUMMARY OF THE INVENTION

The present invention provides a method and composition for treating immune disorders and chronic infections. As used herein, immune disorders include inflammatory conditions, autoimmune diseases, and immune senescence. As used herein, chronic infections and chronic viral infections include viral infections, such as the acquired immune deficiency syndrome (AIDS).

Pursuant to the present invention, a composition including a therapeutically effective amount of an intracellular glutathione stimulator and an omega-3 fatty acid source is administered to the patient. The composition can be administered either enterally or parenterally. For example, the composition can be administered parenterally as an emulsion or enterally as a diet to the patient.

In an embodiment, the present invention provides a method of treating a viral infection comprising the step of administering to a patient having a viral infection a therapeutically effective amount of a composition including an intracellular glutathione stimulator and an omega-3 fatty acid source.

In an embodiment, the present invention provides a method of treating an immune disorder comprising the step of administering to a patient having an immune disorder a therapeutically effective amount of a composition including an intracellular glutathione stimulator and an omega-3 fatty acid source.

In an embodiment, the composition includes: no less than 0.15% of the total calories (.36 g/day/1500 Kcal) as a glutathione stimulator; and no less than 1.5% of the calories (2.5 g/day/1500 Kcal) as omega-3 fatty acid.

In an embodiment, the present invention provides a composition for treating a viral infection comprising a therapeutically effective amount of an intracellular glutathione stimulator and an omega-3 fatty acid source. The ratio of the intracellular glutathione stimulator to omega-3 fatty acid source is approximately 0.05 to about 1.25.

In an embodiment, the present invention provides a composition for treating an immune disorder comprising a therapeutically effective amount of an intracellular glutathione stimulator and an omega-3 fatty acid source. The ratio of the intracellular glutathione stimulator to omega-3 fatty acid source is approximately 0.05 to about 1.25.

In an embodiment, the glutathione stimulator is chosen from the group consisting of: L-2-oxothiazolidine-4-carboxylate; glutathione esters; glutathione; compositions rich in cysteine; and N-acetylcysteine.

In an embodiment, the omega-3 fatty acid source includes marine oil.

Additional features and advantages of the present invention are described in, and will be apparent from, the detailed description of the presently preferred embodiments and from the drawings.

BRIEF DESCRIPTION OF THE DRAWINGS

FIG. 1 illustrates graphically survival, by percent, of mice infected with MAIDS versus age in days for five treatment groups.

DETAILED DESCRIPTION OF THE PRESENTLY PREFERRED EMBODIMENTS

The present invention provides a method of treating a viral infection or immune disorder as well as a composition for same. In an embodiment, a method of treating a viral infection is provided comprising the step of administering to a patient having a viral infection a therapeutically effective amount of a composition including an intracellular glutathione stimulator and an omega-3 fatty acid source.

In an embodiment, a method of treating an immune disorder is provided comprising the step of administering to a patient having an immune disorder a therapeutically effective amount of a composition including an intracellular glutathione stimulator and an omega-3 fatty acid source.

Compositions for treating viral infections and immune disorders are also provided by the present invention. The compositions include a therapeutically effective amount of an intracellular glutathione stimulator and an omega-3 fatty acid source. The ratio of intracellular glutathione stimulator to omega-3 fatty acid source being approximately 0.05 to about 1.25.

Preferably, no less than 0.15% of the total calories of the composition (0.36 g/day/1500 Kcal) is a glutathione stimulator. Preferably, no less than 1.5% of the total calories of the composition (2.5 g/day/1500 Kcal) is omega-3 fatty acid.

The composition of the present invention can be administered either enterally or parenterally. When administered enterally, the composition of the present invention can be part of a diet. In this regard, the oral administration of the composition can include, with respect to the composition for stimulating intracellular glutathione, a cysteine-rich protein, hydrolyzed protein, or short peptide chain. This can include glutathione itself.

As a protein, the intracellular glutathione stimulator must be at least 1.3% by weight cysteine. Therefore, as used herein, a "cysteine-rich protein" means a protein that is at least 1.3% by weight cysteine. This excludes the protein from being merely, casein, total milk product, or soy protein. On the other hand, whey (2.0%), egg white (2.5%), serum albumin (5.5%), and lactalbumin (5.8%) all have sufficient cysteine content, as well as mixtures including same.

Besides cysteine rich proteins, a number of compounds are known for stimulating the intracellular synthesis of glutathione. In addition to glutathione, pursuant to the present invention, other substrates that stimulate intracellular glutathione synthesis can be used. Such substrates include L-2-oxothiazolidine-4-carboxylate, other thiazolidine-4-carboxylate analogs, and glutathione esters.

L-2-oxothiazolidine-4-carboxylate, in vitro, is subjected to the action of 5-oxo-L-prolinase in the presence of adenosine triphosphate to produce S-carboxyl cysteine. S-carboxyl cysteine is then decarboxylated to produce cysteine. Cysteine is then metabolized to provide glutathione. See, U.S. Pat. Nos.: 4,335,210; 4,434,158; 4,438,124; 4,665,082; and 4,647,571 the disclosure of which are incorporated herein by reference.

As previously stated, the non-cysteine substrate can include a glutathione ester. For example, the compound can have the structure:

wherein R is an alkyl group containing 1 to 10 carbon atoms. Preferably, the methyl and ethyl glutathione esters are used. It is also preferred to use glutathione isopropyl ester. Glutathione esters are disclosed in U.S. Pat. No. 4,784,685, the disclosure of which is incorporated herein by reference.

Additionally, N-acetylcysteine can be utilized pursuant to the present invention to stimulate intracellular synthesis of glutathione.

What is important is that the intracellular levels of glutathione are increased pursuant to the method and composition of the present invention.

Additionally, a component of the composition of the present invention includes an omega-3 fatty acid source. Such fatty acid sources can include either an omega-3 fatty acid itself or marine oils such as menhaden, mackerel, algae, herring, blue fish, anchovy, and salmon, which all have significant levels of omega-3 fatty acid.

The omega-3 fatty acid source, of course, lends itself to use as an enteral or parenteral composition. For example, in a parenteral composition, the omega-3 fatty acid source would be present as part of a lipid emulsion. An example of such an emulsion is a 20% (g lipid/100 ml) lipid emulsion in which the triglyceride is derived from marine sources and is naturally enriched in n-3 fatty acids such as eicosapentenoic acid (EPA) and docosahexenoic acid (DHA). Another example would be a 20% (g lipid/100) lipid emulsion prepared from mixed triglyceride sources such as soy oil, marine oil, and medium chain triglycerides. The intent of the latter is to supply a balanced mixture of fatty acids for nutritional benefit.

Omega-3 fatty acids are incorporated into the cell membranes, and also serve as precursors for prostaglandins of the $PG_1$ series, including leukotrienes. These are anti-inflammatory.

Due to the incorporation of the omega-3 fatty acids in the cell membranes, the combination of omega-3 and the glutathione precursor enhances the transport of the glutathione precursor and analogs into the cells. Once in the cells, the glutathione precursors can act in a beneficial anti-oxidant capacity.

Additionally, by reason of the increase production of less inflammatory prostaglandins and anti-inflammatory leukotrienes, there is less inflammatory activation of macrophages, neutrophils, and lymphocytes. Further, there is less production of cytokines and free radicals in view of the omega-3 fatty acids and a reduced need for the anti-oxidant activity of glutathione. The glutathione participates in leukotrienes and prostaglandin synthesis. Thus, the combination of the two components potentiate each other.

By way of example, the composition of the present invention as a parenteral treatment can include a 20% lipid emulsion prepared from triglyceride derived from marine oil or prepared from a mixed triglyceride source obtained by mixing marine oils with vegetable oils such as soy, safflower, rapeseed, or sunflower oil and medium chain triglyceride oils. This lipid emulsion would be administered to a patient parenterally as part of a total parenteral nutrition (TPN) regimen including protein as amino acids, carbohydrates, minerals, and vitamins. The protein component of this parenteral nutrition regimen would be formulated to contain no less than 0.15% of calories as L-2-oxothiazolidine-4-carboxylate, as a part of the amino acid formulations.

Preferably, the ratio of the intracellular glutathione stimulator to omega-3 fatty acid source is approximately 0.05 to about 1.25.

By way of example, the composition of the present invention as an enteral diet could include omega-3 fatty acid as approximately 2% of about 8% of the total calories and approximately 0.1% to 1% as cysteine or other intracellular glutathione stimulator. If, for example, menhaden oil is used as the omega-3 fatty acid source, because menhaden oil contains 21% omega-3 as the % of lipid, approximately 10% to 40% of the diet, by calories, would comprise menhaden oil. Likewise, because whey comprises approximately 2% cysteine, approximately 5% to 50% of the diet, by calories, would comprise whey. The cysteine content of some other products is as follows: glutathione 40%; lactalbumin 5.8%; serum albumin 5.5%; egg white 2.5%; and casein 0.3%. The remaining components of the diet can include other nutrients as set forth in the example.

By way of example and not limitation, an example of the present invention will now be given.

EXAMPLE 1

This experimental design was to measure the benefits of the present invention. Five treatment groups, 40 mice/group, 10 kept uninfected and 30 infected with MAIDS were considered after 8 weeks of the diets. MAIDS exposure was at two viral strengths: 100,000 and 200,000 units/mouse, via single injection.

To study the survival rate of Murine Acquired Immune Deficiency Syndrome (MAIDS) virus injected mice were maintained on the following dietary regimens.
A. Casein 20% by weight as a source of protein and
  (I) Diet containing 20% by weight corn oil
  (II) Diet containing 20% by weight fish oil
B. Lactalbumin 20% as a source of protein and
  (III) Diet containing 20% by weight corn oil
  (IV) Diet containing 20% by weight fish oil
C. Casein 20% and Corn Oil 20% by weight diet -
  (V) Supplemented with 0.1% by weight L-2-oxothiazolidine-4-carboxylate The aim of this study was to compare the effect of two sources of protein and two sources of fat on the proliferation of MAIDS viral infection and survival. The experiments were designed to understand whether viral infection induced by MAIDS could be modulated by the above diets.

Virus: Cell-free virus stock of LpBM5 MukV were prepared and titrated before injection to mice receiving the different diets. Virus stock were injected intraperitoneally in a volume of 0.1 ml after eight weeks of feeding the experimental diets. Virus stock of LpBM5 MuLV was prepared from the filtered supernatant of chronically infected SC-1 cells.

Animals: Special pathogen-free C57BL/6 mice used in the study were obtained from Charles River Breeding Laboratories. Animals were housed in sterile cages and were fed (ad libitum) semi-purified diets described below. All animals were transferred to a clean cage and rack with fresh contact bedding at least once per week. Environmental conditions for the study were maintained at approximately 75° F., 45% RH with 15 air changes per hour and a 12 hour light/12 hour dark cycle.

Animals were monitored upon arrival and monthly thereafter under a surveillance program designed to detect enzootic and epizootic conditions in the mice. Animals which developed intercurrent health problems were evaluated by the in-house staff Veterinary Diagnostic Laboratory.

All persons handling the mice entered the room dedicated to this study through a clean corridor. Animals with viral disease, splenomegaly, or tumors detectable on gross inspection were recorded and saved for pathological examination. Animals were weighed weekly and inspected daily while feeding - 7 days a week.

Diet: The composition of the basal diet is shown in the table. The bulk of the diet, in powder form, was prepared and stored under (nitrogen) at −20° C. Fish oil was added weekly. Care was taken to prevent lipid peroxidation. All diets were stored under nitrogen at −20° C. to prevent oxidation of oil. Diets were provided fresh daily before the dark cycle to decrease the duration exposed to air before consumption. Left over food was discarded.

| COMPOSITION OF BASAL DIET | |
|---|---|
| Ingredient | Weight (% w/w) |
| Vitamin-Free Casein or Lactalbumin | 20.00 |
| Stripped Corn Oil or Fish Oil | 20.00 |
| Corn Starch | 25.05 |
| Sucrose | 25.05 |
| Cellulose | 5.00 |
| D-L Methionine | 0.30 |
| Choline Chloride | 0.10 |
| Salt Mix (AIN-76)[a] | 3.50 |
| Vitamin Mix[b] | 1.00 |

[a]The salt mix was supplemented with 0.0023 mg/kg diet of Na fluoride.
[b]Composition/kg vitamin mix; Vitamin A acetate, 150,000 IU; Vitamin D, 15,000 IU; dl- tocopherol acetate (per experimental design); Vitamin K, 5 mg; biotin, 20 mg; folacin, 200 mg; inositol, 2,380 mg; niacin, 3,000 mg; Ca pantothenate, 1,600 mg; riboflavin, 700 mg; thiamin, 600 mg; Vitamin B6, 700 mg; Vitamin B12, 1 mg; corn starch, up to 1 kg.

All diet components were purchased from ICN, except for the whey protein which was from Quest, but diet mixing was done by the laboratory kitchen.

The attached figure and tables illustrate survival at the time the decision was made to kill all of the remaining survivors (age = 350 days).

TABLE 1

MAIDS TRIAL - LIFE-SPAN (DAYS)*
HIGH VIRUS DOSE

| # | I:<br>CO/CA | II:<br>FO/Ca | III:<br>CO/Whey | IV:<br>FO/Whey | V:<br>CO/Ca/P |
|---|---|---|---|---|---|
| 1 | 156 | 156 | 167 | 167 | 159 |
| 2 | 156 | 156 | 168 | 174 | 161 |
| 3 | 156 | 161 | 176 | 175 | 161 |
| 4 | 158 | 165 | 179 | 176 | 170 |
| 5 | 160 | 167 | 181 | 182 | 184 |
| 6 | 162 | 176 | 185 | 184 | 185 |
| 7 | 174 | 182 | 190 | 185 | 189 |
| 8 | 181 | 189 | 193 | 193 | 189 |
| 9 | 181 | 190 | 200 | 197 | 197 |
| 10 | 182 | 193 | 203 | 198 | 207 |
| 11 | 182 | 204 | 203 | 203 | 212 |
| 12 | 193 | 207 | 210 | 231 | 231 |
| 13 | 198 | 235 | 212 | 246 | 238 |
| 14 | 239 | 262 | 218 | 268 | 264 |
| 15 | 322 |  | 329 |  |  |
| Med= | 181 | 189 | 193 | 193 | 189 |
| (n)= | (15) | (15) | (15) | (15) | (15) |

TABLE 2

LOW VIRUS DOSE - LIFE-SPAN (DAYS)*

| # | I:<br>CO/Ca | II:<br>FO/Ca | III:<br>CO/Whey | IV:<br>FO/Whey | V:<br>CO/Ca/P |
|---|---|---|---|---|---|
| 16 | 199 | 184 | 181 | 210 | 206 |
| 17 | 199 | 193 | 181 | 225 | 215 |
| 18 | 213 | 196 | 185 | 229 | 233 |
| 19 | 214 | 222 | 198 | 262 | 253 |
| 20 | 224 | 234 | 207 | 264 | 260 |
| 21 | 229 | 253 | 214 |  | 274 |
| 22 | 241 | 281 | 218 |  |  |
| 23 | 248 | 313 | 218 |  |  |
| 24 | 257 |  | 238 |  |  |
| 25 | 304 |  | 263 |  |  |
| 26 |  |  | 312 |  |  |
| 27 |  |  |  |  |  |
| 28 |  |  |  |  |  |
| 29 |  |  |  |  |  |
| 30 | — |  |  |  | —** |
| Med= | 248 | 313 | 218 |  |  |
| (n)= | (30) | (29) | (30) | (30) | (29) |

CO - Corn oil (20% by weight)
FO - Fish oil (20% by weight)
CA - Casein (20% by weight)
Whey - Whey Protein (20% by weight)
P - L-2-oxothiazolidine-4-carboxylate (.1% by weight)
*Injected with MAIDS virus at 85 days old (15 Oct. 1990)
**One mouse killed because of misaligned, overgrown teeth.
***One mouse died at 111 days without showing typical lymph node enlargement of MAIDS.

In the high virus dose study, there was a trend, although perhaps not statistically significant, for longer survival in the FO/Whey group over CO/Ca. In the low virus dose study, fish oil and whey together resulted in better survival than corn oil and casein (<0.025), but fish oil alone (II) or whey alone (III) did not show significant benefits.

By way of example, and not limitation, contemplative examples of the present invention will now be given.

CONTEMPLATIVE EXAMPLE NO. 1

Fifteen teenagers and young adults (13-28years) with a history of systemic lupus erythematosus (SLE) were receiving intermittent immunosuppressive adrenocortical steroid therapy to control flare-ups of their autoimmune condition. After each acute episode was brought under control, their corticosteroid dose was gradually reduced over a period of weeks to months. During the periods of drug treatment, the subjects suffered from some of the typical adverse reactions of steroids: increased susceptibility to infection, fluid and electrolyte disturbances, hyperglycemia and others.

Under the advice and supervision of their physician, the subjects modified their diets to incorporate half of their caloric intake in the form of an oral enteral supplement which contains 16% of its total calories as whey protein and 15% of total calories as a marine oil containing approximately 21% omega-3 fatty acids.

Over the course of two years of observation of these subjects, they collectively had 27% fewer SLE flare-ups requiring hospitalization compared to a control group continuing with their typical diet. Furthermore, the flare-ups of the experimental group required less use of steroids to bring under control, and the subjects needed smaller doses over a shorter period of time to regain remission.

CONTEMPLATIVE EXAMPLE NO. 2

A 36-year old HIV+male patient presented at an in-hospital AIDS clinic with chronic diarrhea, thrush, lymphadenopathy, and weight loss of 35 pounds in two months (approximately 20%). Symptomatic treatment was undertaken including antidiarrheal medication and dietary counseling. The hospital dietary staff recommended feeding a standard enteral formulation administered by nasogastric tube. When seen at the clinic three weeks later, the patient had lost an additional four pounds and report continuing diarrhea.

The enteral formula was changed to a formulation that contained 16% of calories as whey protein to increase the availability of the glutathione precursor cysteine. The new formulation contained a modified lipid content so that 16% of the calories were as a marine oil. The subject was advised to continue administration by nasogastric tube.

When next seen at the clinic 24 days later, the patient reported a greatly improved gastrointestinal function with only rare episodes of diarrhea. He had gained 6 pounds and also reported that the pain associated with the swollen lymphoid tissue was greatly diminished. At the patient's request, nasogastric feeding was discontinued and the whey protein/marine oil formulation was continued as a supplement to a dietary plan devised by the dietary staff.

At the subsequent visits to the clinic over the next four months, the subject reported only rare episodes of diarrhea. Weight gain continued.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A composition for treating immune disorders, inflammation, and or chronic infections comprising:
   an intracellular glutathione stimulator chosen from the group consisting of: L-2-oxothiazolidine-4-carboxylate, glutathione, and glutathione esters; and
   an omega-3 fatty acid source comprising at least 1.5% of the total calories.

2. The composition of claim 1 wherein the glutathione stimulator comprises at least 0.15% of the total calories of the composition.

3. The composition of claim 1 wherein the ratio of intracellular glutathione stimulator to omega-3 fatty acid source by calories, is from about 0.05 to about 1.25.

4. The composition of claim 1 wherein the omega-3 fatty acid source comprises marine oil.

5. The composition of claim 4 wherein the marine oil is chosen from the group consisting of: menhaden oil; mackerel oil; algae oil; herring oil; blue fish oil; anchovy oil; and salmon oil.

* * * * *